(12) United States Patent
Terblanche et al.

(10) Patent No.: US 11,272,919 B2
(45) Date of Patent: Mar. 15, 2022

(54) METHOD OF PASSING A SUTURE THROUGH A PLANTAR PLATE

(71) Applicant: TRIMED, INCORPORATED, Santa Clarita, CA (US)

(72) Inventors: Ignatius Petrus Stefanus Terblanche, Milnerton (ZA); Jacques Marais, Durbanville (ZA); Jacobus Frederick Janse Van Vuuren, Saldanha (ZA); Stephan Janse Van Vuuren, Saldanha (ZA)

(73) Assignee: TriMed, Incorporated, Santa Clarita, CA (US)

( * ) Notice: Subject to any disclaimer, the term of this patent is extended or adjusted under 35 U.S.C. 154(b) by 310 days.

(21) Appl. No.: 16/472,066

(22) PCT Filed: Dec. 18, 2017

(86) PCT No.: PCT/IB2017/058036
§ 371 (c)(1),
(2) Date: Jun. 20, 2019

(87) PCT Pub. No.: WO2018/116113
PCT Pub. Date: Jun. 28, 2018

(65) Prior Publication Data
US 2020/0085424 A1   Mar. 19, 2020

(30) Foreign Application Priority Data
Dec. 21, 2016   (ZA) ................................ 2016/08790

(51) Int. Cl.
*A61B 17/04* (2006.01)
*A61B 17/00* (2006.01)

(52) U.S. Cl.
CPC *A61B 17/0482* (2013.01); *A61B 2017/00743* (2013.01)

(58) Field of Classification Search
CPC ...... A61B 17/0482; A61B 2017/00743; A61B 17/0483; A61B 17/0218; A61B 17/1682; A61B 17/7291
See application file for complete search history.

(56) References Cited

U.S. PATENT DOCUMENTS

2004/0122471 A1   6/2004   Toby et al.
2013/0178938 A1   7/2013   Fallin et al.
(Continued)

FOREIGN PATENT DOCUMENTS

WO   2004058053 A2   7/2004
WO   2004112619 A1   12/2004

OTHER PUBLICATIONS

International Search Report, dated Mar. 19, 2018 in International Patent Appln. No. PCT/IB2017/058036.
(Continued)

*Primary Examiner* — Brooke Nicole Labranche
(74) *Attorney, Agent, or Firm* — Wood, Phillips, Katz & Mortimer

(57) ABSTRACT

The invention provides a plantar plate repair device to facilitate the appropriate placement of sutures during a plantar plate repair. The device comprises a shaft terminating in a footprint projecting angularly from the shaft, the footprint further defining an opening through which a needle is threadable. The shaft further includes a guide slidable on the shaft to operatively clamp the plantar plate between the guide and footprint. A needle receiving guide hole is provided on the guide to operatively guide a needle through the opening in the footprint to pass a length of suture from the needle through the plantar plate.

21 Claims, 8 Drawing Sheets

(56) References Cited

U.S. PATENT DOCUMENTS

2013/0184818 A1 7/2013 Coughlin et al.
2013/0231669 A1 9/2013 Sinnott et al.

OTHER PUBLICATIONS

Examiner Report No. 1, dated Aug. 24, 2020 in Australian Patent Application No. 2017380830.
Office Action dated Apr. 19, 2021 in Canadian Patent Application No. 3,048,161.
Extended European Search Report, dated Nov. 6, 2020 in European Patent Application No. EP 17 88 2964.

METHOD OF PASSING A SUTURE THROUGH A PLANTAR PLATE

FIELD OF INVENTION

This invention relates to a plantar plate repair device for repairing the plantar plate of the foot/toe, more particularly to repair an injury or tear of the plate using a dorsal approach.

BACKGROUND OF INVENTION

The plantar plate is a thick supporting ligament structure found in the metatarsophalangeal (MTP) and interphalangeal (IP) joints. This ligament provides stability to the toes by keeping the toes in place and stops them from over-extending or drifting.

Injury to the plantar plate or plantar plate tears is fairly common and refers to the disruption to any of the plantar plates of the foot, most commonly on the second toe.

Surgical procedure for a plantar plate repair can be done either from a plantar or dorsal approach.

The dorsal approach has been found to include many advantages over the plantar approach, especially in that a patient can bear weight on the foot after about 48 hours of surgery and that the correction tends to be solid. Employing a dorsal approach and combining Weil's osteotomy is well known in the art and usually comprises a number of steps including: performing a Weil's osteotomy allowing the capital fragment to be recessed under the metatarsal; digital distraction by a distraction clamp over K-wires; assessing the plantar plate and repairing same by passing a suture through the plantar plate; followed by the step of repairing the plantar plate back to the proximal phalanx.

The success of this procedure depends greatly on the ability to place the suture in the plantar plate correctly. This often proves fairly difficult because the dorsal approach results in soft tissue limitations meaning the space is confined. The confined space further necessitates retraction of soft tissue.

A plethora of methods and tools have been developed to facilitate the placing of this suture in a convenient and accurate manner. The most common is by employing the various devices described in US2013/0184818 including a suture passing instrument such as the Mini Scoprion DX™ needle or a set of Micro Suture Lassos™.

These devices are however expensive due to the complex nature thereof. The procedure in placing the suture is also prone to human error as the surgeon is required to place these sutures by hand and onto an unstabilised plantar plate. Operating in a confined space aggravates this difficulty.

The Weil's osteotomy presently forms an integral and unavoidable part of a plantar plate repair procedure. As this procedure is fairly complex in nature, it may lead to complications.

Another method and device to assist in placing and retrieving the suture is to shape the ends of a K-wire or "paperclip" type wire into a shape substantially corresponding to the shape of a circle which is then placed underneath the plantar plate. The suture is then passed through this formed "circle" and the suture retrieved by pulling the circle from under the plantar plate to a position above the foot. This device has however proven unsatisfactory in that the placing of the sutures are still prone to human error and only assist the surgeon in retrieving the suture once passed through the plantar plate. A further disadvantage of this device is that the plantar plate is not stable during the step of passing the suture. It is furthermore difficult to provide repeatable results in bending and shaping the K-wire/paper-clip. Bending of the K-wire/paper-clip also makes this device unsatisfactory for its purpose, or at least makes it incapable for reuse.

OBJECT OF THE INVENTION

It is accordingly an object of the present invention to provide a plantar plate repair device with which the above disadvantages could at least partially be overcome or alleviated and/or to provide a more useful alternative to the known devices.

SUMMARY OF INVENTION

In accordance with a first aspect of the invention there is provided a plantar plate repair device comprising a shaft terminating in a footprint projecting angularly from the shaft, the footprint further defining an opening through which a needle is threadable, the shaft further including a guide slidable on the shaft to operatively clamp the plantar plate between the guide and footprint, the guide further defining at least one needle receiving guide hole for operatively guiding a needle through the opening in the footprint to pass a length of suture from the needle through the plantar plate.

The invention further provides for the footprint to project from the shaft at an angle of between 90 and 150 degrees, preferably between 115 and 150 degrees.

The invention yet further provides for the footprint to terminate in a sharp bevelled end; and preferably for the end of the footprint to be pointed or flat.

There is yet further provided for the shaft to be configured as a rail which operatively receives gripping formations of the guide, and for the shaft to be notched, preferably proximate the handle, such that the guide is slidably insertable and removable therefrom. Alternatively, the shaft is provided with a slot disposed substantially centrally on the shaft, which operatively receives gripping formations of the guide to allow sliding of the guide within the slot and along the shaft. The slot may further be enlarged proximate the handle such that the guide is slidably insertable and removable therefrom.

Further to the invention, the guide is provided with a slot which extends longitudinally from the needle receiving guide hole and opens to a front of the guide such that the suture can be disengaged from the guide. Alternatively, the needle receiving guide hole comprises a pair of connected receiving guide holes for operatively guiding a pair of needles through the opening in the footprint to loop a length of suture from the needle through the plantar plate.

The invention further provides for the guide to further include gripping formations, preferably gripping teeth on an operatively lower surface. The guide may further include gripping means such as notches or indentations on the sides of the guide to facilitate gripping during sliding movement of the guide.

The width of the shaft, guide and footprint may be provided as equal to or wider than the plantar plate, preferably 14 mm to 16 mm.

The invention also provides for a handle to extend from the shaft proximate an end opposite the footprint; and preferably for the handle to project between 90 and 150 degrees, preferably 115 and 150 degrees from the shaft.

The invention further provides for the shaft and footprint to be formed from a flat sheet of surgical steel.

In accordance with a second aspect of the invention, there is provided for a guide in accordance with the first aspect of the invention for use in repairing a plantar plate injury.

In accordance with a third aspect of the invention there is provided a plantar plate repair device for use in repairing a plantar plate injury.

In accordance with a fourth aspect of the invention, there is provided for a method of passing a suture through a plantar plate comprising the steps of:

providing a plantar plate repair device in accordance with the first aspect of the invention;

placing the footprint underneath the plantar plate such that the plantar plate is located on the footprint;

sliding the guide into engaging with the plantar plate to operatively stabilise the plantar plate;

passing opposite ends of a suture through the guide hole, the plantar plate and the opening in the footprint respectively to form a suture loop; pulling said loop to locate on the plantar plate; and removing the footprint and associated ends of the suture from below the plantar plate and pulling said footprint dorsally to operatively pull the ends of the suture to above the plantar plate.

The invention further provides for the step of passing the opposite ends of the suture through the guide hole, the plantar plate and the opening in the footprint respectively to form a suture loop to comprise of:

a first step of passing one end of the suture through the guide hole, plantar plate and opening in the footprint, and a second step of re-aligning the device relative to the plantar plate and passing the other end of the suture through guide hole, plantar plate and opening in the footprint.

BRIEF DESCRIPTION OF DRAWINGS

The invention will now be described further by way of non-limiting examples, with reference to the accompanying drawings wherein.

Figure 1:
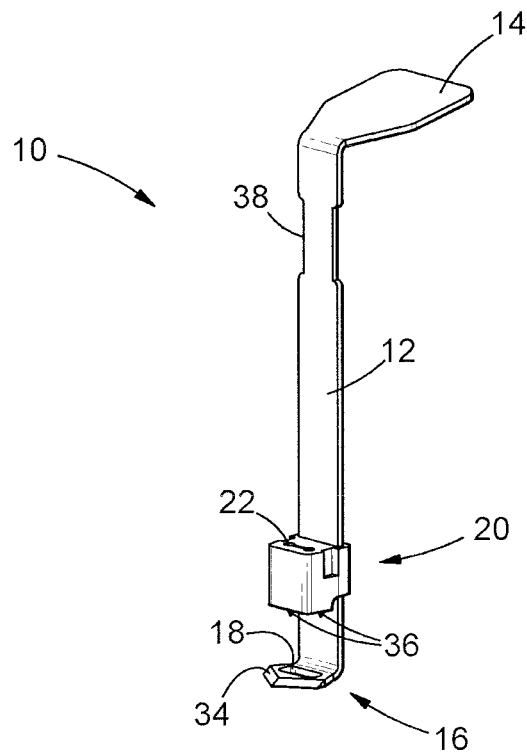
FIG. 1 illustrates a top perspective view of a plantar plate repair device in accordance with a first embodiment of the invention.
Figure 2:
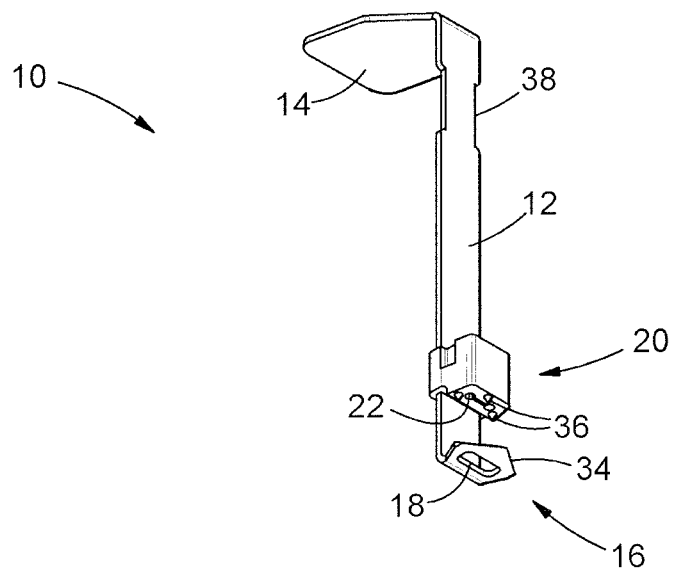
FIG. 2 is a bottom perspective view of the device of FIG. 1.
Figure 3:
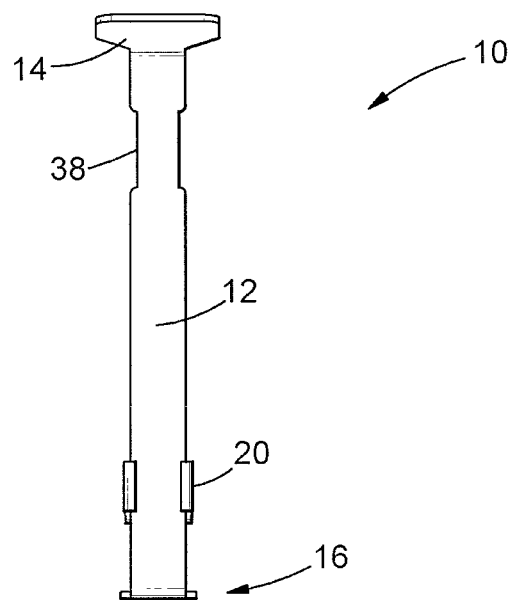
FIG. 3 is a back side view of the device of FIG. 1.
Figure 4:
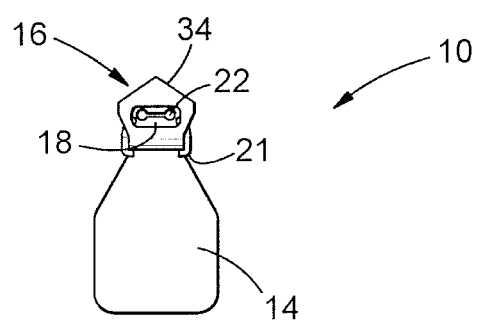
FIG. 4 illustrates a bottom plan view of the device of FIG. 1.
Figure 5:
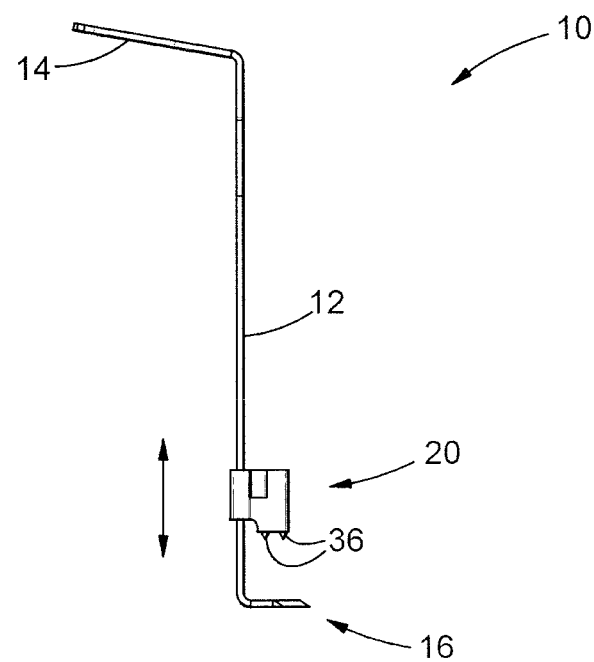
FIG. 5 is a side plan view of the device of FIG. 1.
Figure 6:
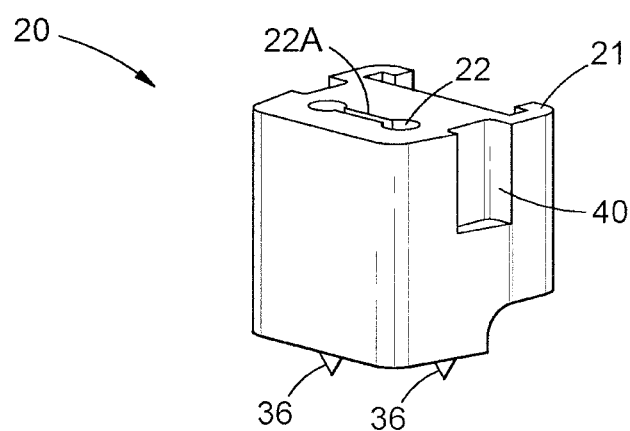
FIG. 6 shows a guide according to another aspect of the invention.
Figure 7:
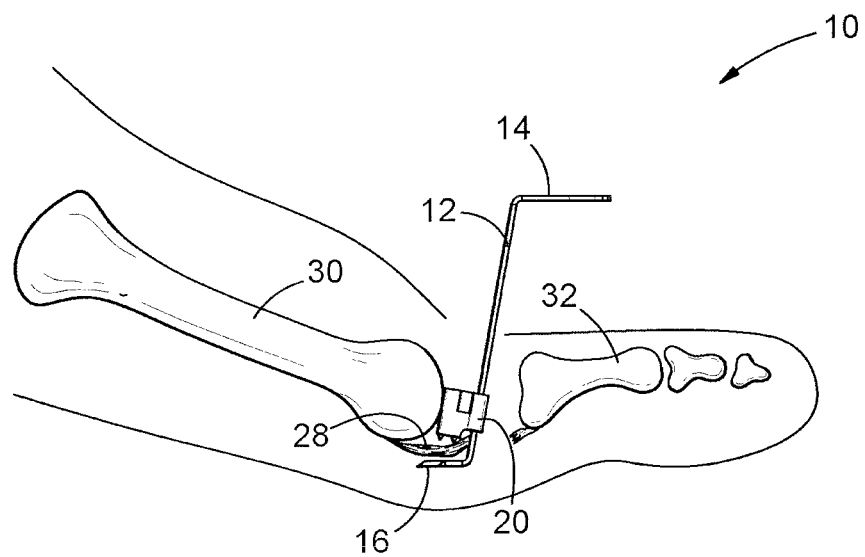
FIGS. 7-11 show the plantar plate repair device of FIG. 1 in various stages of operation in repairing a plantar plate.
Figure 8:
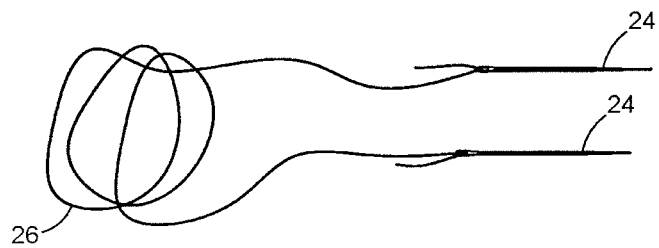
Figure 9:
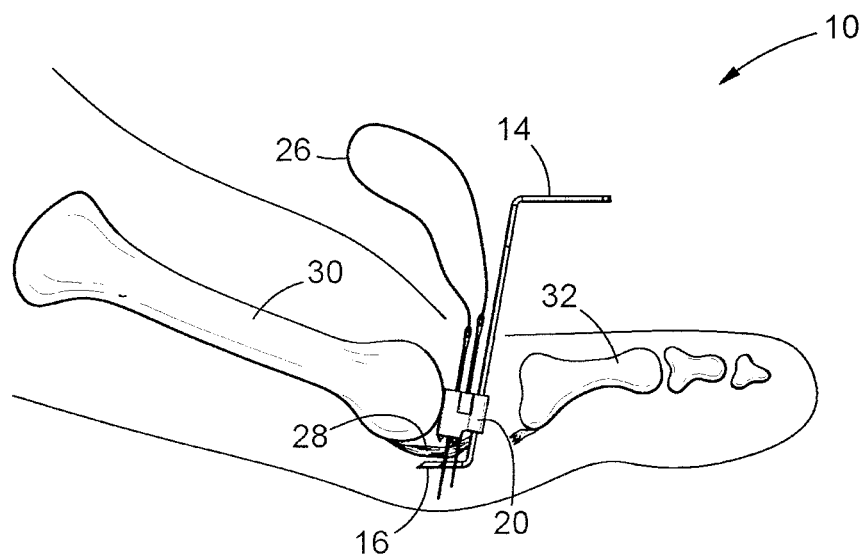
Figure 10:
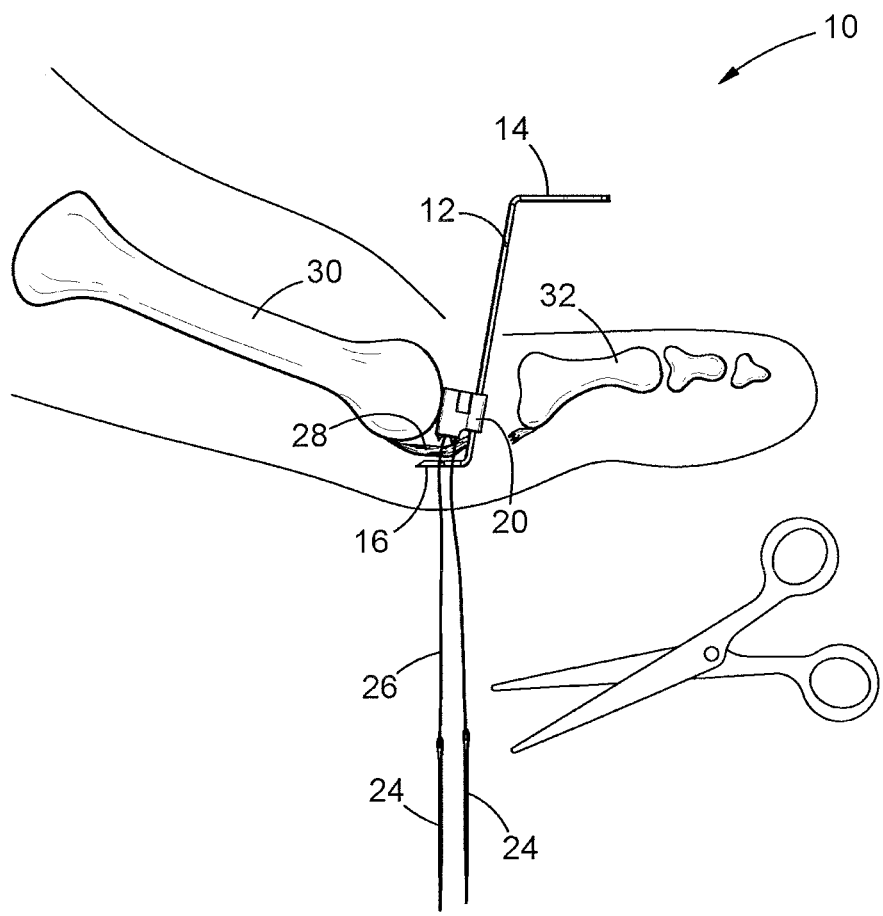

The presently disclosed subject mailer will now be described more fully hereinafter with reference to the accompanying figures, in which representative embodiments are shown. The presently disclosed subject matter can, however, be embodied in different forms and should not be construed as limited to the embodiments set forth herein.

Rather, these embodiments are provided so that this disclosure will be thorough and complete, and will fully convey the scope of the embodiment to those skilled in the art.

DESCRIPTION OF PREFERRED EMBODIMENTS OF THE INVENTION

With reference to the drawings, a plantar plate repair device for repairing the plantar plate of the foot/toe according to the invention is generally designated by reference numeral 10.

The plantar plate repair device 10 comprises a shaft 12 which projects from a manipulating handle 14 on one side thereof. On the opposite side, the shaft 12 terminates in a footprint 16 which projects angularly from the shaft 12. The footprint 16 defines an opening 18 through which a needle and suture is threadable as will be described in more detail below. A guide 20 is slidable on the shaft 12 by means of gripping formations 21 of the guide 20 to act as a guide for the needle and suture as will be explained in more detail below.

According to a first embodiment of the invention shown in FIGS. 1 to 6, the guide 20 has a pair of needle receiving guide holes 22 for operatively guiding the needle and suture through the plantar plate and opening 18 of the footprint 16 respectively to form a loop of suture on the plantar plate. In this respect, and shown in detail in FIG. 6, the guide holes 22 are connected by a channel 22A to ensure that the loop of suture is passable through the guide 20 as will be evident from the description which follows below. The guide 20 furthermore acts as a clamp, in use, by clamping the plantar plate between an operatively lower surface of the guide 20 and the footprint 16.

The shaft 12, handle 14 and footprint 16 is manufactured from a flat sheet of surgical stainless steel. The overall width of these components is equal to or wider than the plantar plate, preferably around 14 to 16 millimetres but can be varied if required. The guide 20 is manufactured from any suitable medical grade plastics material.

The operation of the plantar plate repair device will now be described and illustrated.

Firstly, the known procedures to a dorsal approach are followed by making a dorsal longitudinal incision either in the interspace, or directly over the MTP joint. The MTP joint is distracted and K-wires are fixed on both sides of the joint. The deforming contracted capsule is released to free up the plantar plate. The insertion site of the ligament is roughened/denuded to promote healing. The aforementioned procedures are well known in the art and are accordingly not provided with unnecessary detail for the sake of brevity.

These procedures are now followed by the procedure wherein the surgeon passes the suture through the plantar plate and is best illustrated in FIGS. 7 to 11 which are diagrammatic representations of the various steps in accordance with the invention.

By using the plantar plate repair device 10, the surgeon inserts the plantar plate repair device 10 into the MTP joint between the metatarsal 30 and phalanx 32 of the patient such that the device 10 locates underneath the plantar plate 28. In this respect, the footprint 16 is located below the plantar plate 28 as shown such that the opening 18 of the footprint 16 is located at the location where the suture is to be passed.

The guide 20 is then slid downwards on the shaft 12 towards the plantar plate 28 to clamp said plantar plate 28 and footprint 16. Gripping formations in the form of gripping teeth 36 disposed on the operatively lower surface of the guide 20 facilitates the gripping and clamping of the plantar plate 28 to ensure that the plantar plate is conveniently fixed and stabilised at the preferred location. In this respect the guide 20 acts as a plantar plate stabiliser and maintains the required tension of the plantar plate when passing the needle and suture therethrough.

The tip 34 of the footprint 16 is furthermore bevelled and pointed/triangular to provide a sharp tip which can be used to separate the plantar plate from the flexors of the foot as well as to dissect any unwanted tissue in the operating process. The footprint 16 therefore acts as a dissector to create the correct anatomical plane. The edges of the opening 18 of the footprint 16 are however smooth and rounded, so as not to inadvertently damage or sever the suture during use the device 10.

Once the plantar plate 28 is securely clamped as described, the surgeon utilizes a pair of needles 24 and a length of suture 26. Each of the needles 24 and its associated end of the suture 26 is passed through its respective needle receiving guide holes 22, the plantar plate 28 and the opening 18 in the footprint 16—see FIGS. 9 and 10.

The channel 22A which connects the holes 22 enables the loop of suture 26 to be passed through the guide 20 to locate on the plantar plate 28. If required, the guide 20 may be slid upwards on the shaft 12 in order for the surgeon to view the suture 26 placed on the plantar plate 28. Oppositely disposed notches 38 are provided on the shaft 12, proximate the handle 14, should the surgeon wish to remove the guide 20 completely from the device 10. In this instance it is also possible that the guide 20 be removed, in tote, before the suture is passed through the plantar plate 28 and opening 18—this may happen in the very unusual instances where space is limited to such extent that the guide 20 cannot be accommodated or where the location of the suture is unusual.

Notches or indentations 40, closed or open, are also provided on the sides of the guide 20, to provide a convenient gripping means by which a surgeon can manipulate the guide by using pincets to engage said notches 40 to facilitate sliding the guide up and down the shaft 12 of the device 10. This is particularly useful when the guide 20 needs to be placed in, or withdrawn from its clamped position mentioned above, and where space is particularly confined.

Once the ends of the suture 26 are passed through all the components and the sole of the patient's loot, the needles 24 are separated from the ends of the suture 26. In this way, the loop of suture 26 locates on the plantar plate 28, while the ends of the suture 26 are disposed underneath the foot of the patient—see FIG. 10.

Figure 11:
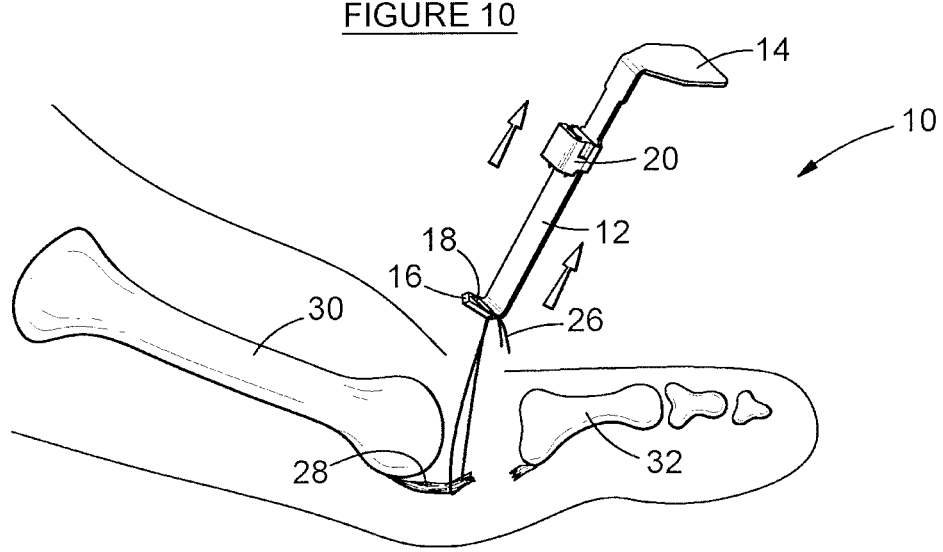

As shown in FIG. 11, the surgeon proceeds to lift the plantar plate repair device 10 (and the suture 26 which is located in the opening 18) from below the plantar plate 28 and pulling said footprint 16 dorsally to operatively pull the ends of the suture 26 to above the plantar plate 28 of the patient. This mechanism is a convenient method of pulling the ends of the suture 26 to above the plantar plate 28, thereby enabling the rest of the procedures in the plantar plate repair to be finalised. These procedures result in the suture ends being fixed to the proximal phalanx by employing one of two known methods. The first known method is by making drill holes on the medial and lateral aspects of the proximal phalanx and to bring the sutures through the drill holes to secure the plantar plate in that fashion. Alternatively, a single drill hole is made in the proximal phalanx, threading both ends of the suture through said hole and fixing the ends of the sutures on the dorsal aspect of the phalanx over a mechanical bridge of a stainless steel button. These procedures are not repeated herein as it is known in the art.

It will however be understood that the invention may be varied without departing from the scope of the invention.

Figure 12:
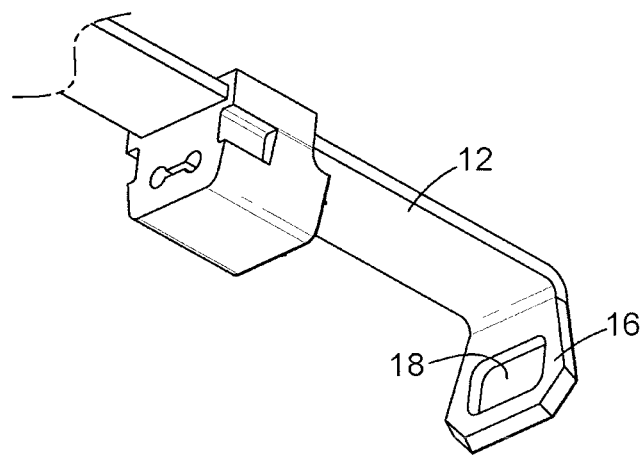
FIG. 12 shows a top perspective view of a footprint of the device in accordance with another embodiment of the invention.

For example, as shown in FIG. 12, the front end of the footprint 16 is flat, thereby increasing the extent to which the footprint 16 can be advanced under the plantar plate. In this embodiment, the front end is also bevelled/sharp to facilitate separation of the plantar plate from the flexors of the foot as well as to dissect any unwanted tissue in the operating process.

Figure 13:
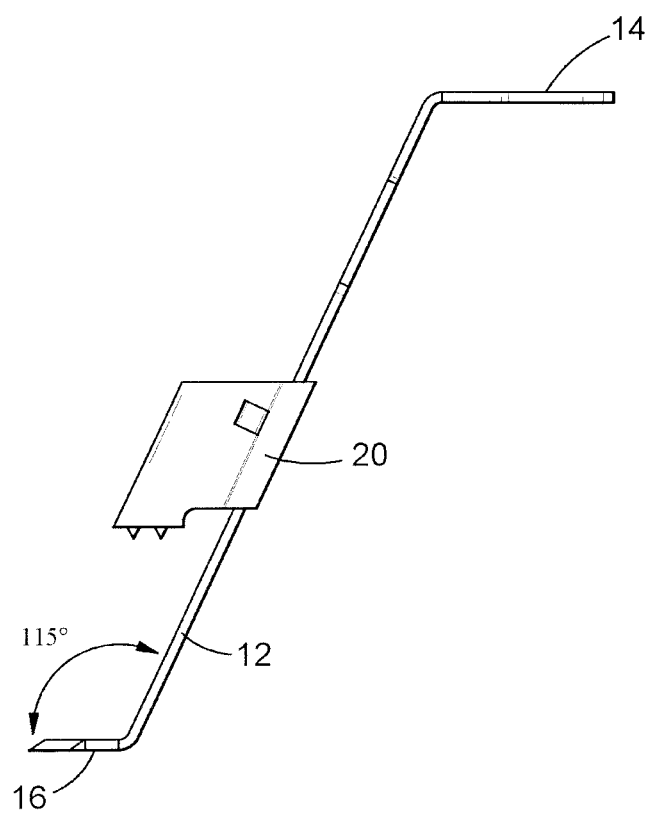
FIG. 13 is a side view of a plantar plate repair device in accordance with another embodiment of the invention.

The angle at which the footprint 16 projects from the shaft 12 can also be varied between 90 and 150 degrees. In the embodiment shown in FIG. 13, the angle is around 115 to 150 degrees. These angles ease manipulation of the device 10 by the surgeon, particularly providing more leverage to enable the surgeon to advance the footprint 16 even further underneath the plantar plate 28. These angles furthermore provide a clearer view of the space around the device 10. It will also be understood that the relative angle of the operatively lower surface of the guide 20 will correspond to the angle at which the footprint 16 projects from the shaft 12, so that the clamping action as described above can be maintained. In addition, the handle will also project at the relative angle to correspond with the particular angular extension of the footprint.

Figure 14:
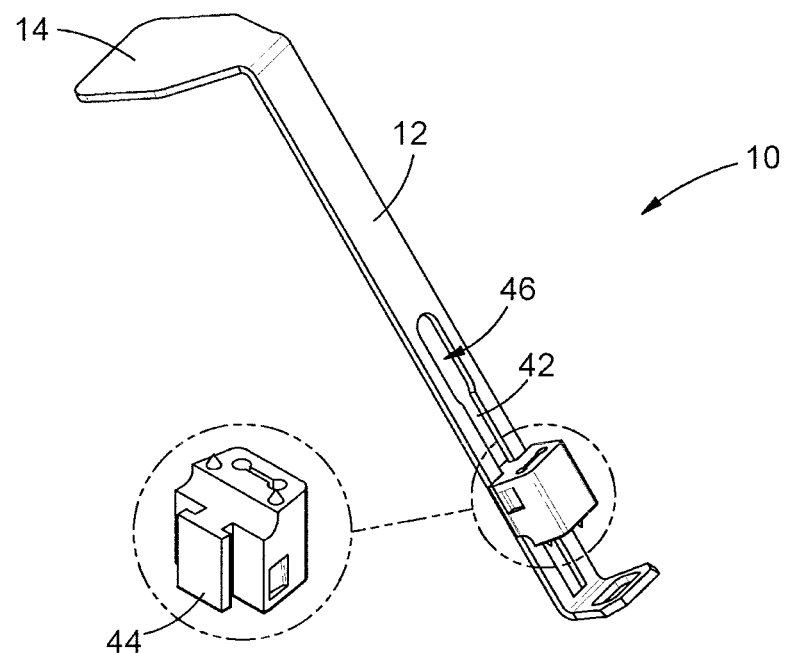
FIG. 14 shows a plantar plate repair device in accordance with another embodiment of the invention.

In a yet further variation of the invention, the sliding movement of the guide 20 can be provided as shown in FIG. 14. In this embodiment, a slot 42 is disposed centrally on the shaft 12 to receive gripping formations 44 on the guide 20. This enables the guide 20 to slide within the slot 42 and along the shaft 12 to fulfill the function described above. The slot 42 is furthermore enlarged at 46 proximate the handle 14 to enable the guide 20 to be inserted and removed from the slot 42 as required.

Figure 15:
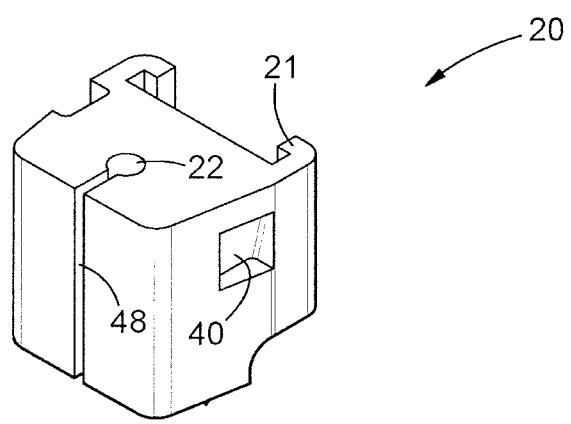
FIG. 15 shows a top perspective view of a guide according to another embodiment of the invention.
Figure 16:
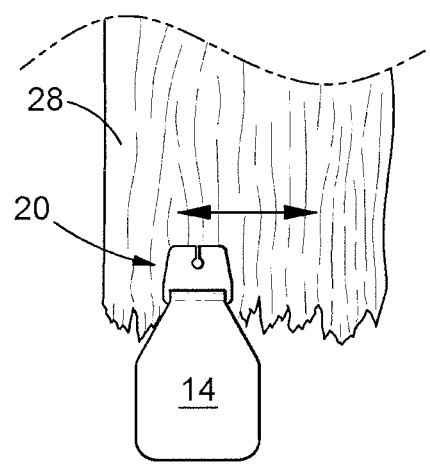
FIG. 16 illustrates a top view of the plantar plate repair device over a plantar plate.

As shown in FIG. 15, the guide 20 may include a single needle receiving guide hole 22 which has a slot 48 extending longitudinally from the needle receiving guide hole 22 and which opens to a front of the guide 20 such that the suture can be disengaged from the guide 20. In this respect, a single needle and suture end is threaded through the plantar plate 28 and footprint 16. The length of suture which is still located within the guide 20, is now passed through the slot 48 so that the guide 20 is freed of this length of suture. The guide 20 may now be slid upwards to unclamp the plantar plate 28 to enable the device 10 to be adjusted or re-aligned to where the second end of the suture is to be passed through the plantar plate 28. Once this position is ascertained, the guide 20 is again clamped at said position and the process of placing the second end of the suture is completed as above. This provides the added benefit of varying the position and therefore the length of the suture, giving the surgeon more freedom to ensure the optimal stitch to be placed on the plantar plate. This is shown in FIG. 16.

It is accordingly asserted that the invention at least partially alleviates the aforementioned disadvantages.

The guide 20, acts as a spacer in the MTP joint and accordingly facilitates the retraction of tissue in order for the surgeon to access the plantar plate. The device according to the invention is furthermore versatile in that, in some instances, a surgeon may elect to avoid a Weil's osteotomy and its associated risks to the patient. In this respect, the angle of attack from above (versus the substantially lateral approach of the prior art procedures), means that a Weil's osteotomy is not required should enough space be available. It will be envisaged however that the Weil's osteotomy can yet be employed in instances where space is limited or should the surgeon prefer to include said procedure in the plantar plate repair. The slidability of the guide 20 furthermore operates as a stabilising clamp and is detachable if required. The guide holds 22 furthermore enables the surgeon to place the suture in the correct location and standardises the stitch footprint, decreasing human error accordingly, whilst still allowing the surgeon freedom where required.

The sharp bevelled tip of the footprint 16, whether pointed or flat, furthermore acts as a convenient dissecting tool and facilitates the advancement and the extent of advancement of the footprint 16 underneath the plantar plate 28.

The flat profile of the device 10, is furthermore space efficient and usable in confined space associated with the present surgical procedure. In addition, the substantially orthogonal/right angles of the footprint, shaft and handle optimise the angle of attack required for a dorsal approach.

Accordingly, the device according to the invention provides a convenient and simple, yet sufficient tool which can be used in repairing a plantar plate.

It will be appreciated by those skilled in the art that the invention is not limited to the precise details as described herein and that many variations are possible without departing from the scope and spirit of the invention. For example, a single needle can be utilized to form the loop of suture as described above, without departing from the scope of the invention. The length of the handle and shaft, as well as the angle at which the handle projects from the shaft can also be varied. The various embodiments of the components described above can also be varied in the device 10 without departing from the scope of the invention.

The description is presented in the cause of providing what is believed to be the most useful and readily understandable description of the principles and conceptual aspects of the invention. In this regard, no attempt is made to show structural details of the invention in more detail than is necessary for a fundamental understanding of the invention. The words used here should be interpreted as words of description rather than words of limitation.

The invention claimed is:

1. A method of passing a suture through a plantar plate comprising the steps of:
    obtaining a plantar plate repair device comprising a shaft with a length, a footprint projecting away from the shaft at an angle to the shaft length, and a guide;
    placing the footprint underneath the plantar plate such that the plantar plate is located directly against the footprint;
    changing a relationship between the footprint and the guide so that the guide directly overlies the plantar plate such that the plantar plate is operatively stabilized between the footprint and the guide; and
    with the plantar plate stabilized, passing a length of a suture through the plantar plate.

2. The method of passing a suture through a plantar plate according to claim 1 wherein the step of passing a length of a suture through the plantar plate comprises passing opposite ends of the length of the suture through the footprint to form a suture loop.

3. The method of passing a suture through a plantar plate according to claim 2 further comprising a step of moving the footprint and associated ends of the suture from below the plantar plate and pulling said footprint dorsally to thereby pull the opposite ends of the suture to above the plantar plate.

4. The method of passing a suture through a plantar plate according to claim 1 wherein the footprint defines an opening, the step of passing a length of a suture through the plantar plate comprises using a needle to pass the suture through the opening in the footprint, the step of changing a relationship between the footprint and guide comprises sliding the guide on the shaft to operatively clamp the plantar plate between the guide and the footprint, and wherein the guide further defines at least one needle receiving guide hole for operatively guiding the needle through the opening in the footprint as the length of suture from the needle is passed through the plantar plate.

5. The method of passing a suture through a plantar plate according to claim 4, wherein the step of obtaining a plantar plate repair device comprises obtaining a plantar plate repair device wherein the footprint projects from the shaft at an angle of between 90 and 150 degrees.

6. The method of passing a suture through a plantar plate according to claim 4, wherein the step of obtaining a plantar plate repair device comprises obtaining a plantar plate repair device wherein the footprint terminates in a sharp beveled end.

7. The method of passing a suture through a plantar plate according to claim 6, wherein the step of obtaining a plantar plate repair device comprises obtaining a plantar plate repair device wherein an end of the footprint is pointed or flat.

8. The method of passing a suture through a plantar plate according to claim 4, wherein the step of obtaining a plantar plate repair device comprises obtaining a plantar plate repair device wherein the shaft is configured as a rail which operatively receives gripping formations of the guide to allow sliding of the guide along the shaft.

9. The method of passing a suture through a plantar plate according to claim 4, wherein the step of obtaining a plantar plate repair device comprises obtaining a plantar plate repair device wherein the shaft is notched and a graspable handle extends from the shaft, wherein the shaft is notched proximate the handle, such that the guide is slidably insertable and removable therefrom.

10. The method of passing a suture through a plantar plate according to claim 4, wherein the step of obtaining a plantar plate repair device comprises obtaining a plantar plate repair device wherein the shaft is provided with a slot disposed substantially centrally on the shaft, which operatively receives gripping formations of the guide to allow sliding of the guide within the slot and along the shaft.

11. The method of passing a suture through a plantar plate according to claim 4, wherein the step of obtaining a plantar plate repair device comprises obtaining a plantar plate repair device wherein the guide is provided with a slot which extends longitudinally from the at least one needle receiving guide hole and opens to a front of the guide such that the suture can be disengaged from the guide.

12. The method of passing a suture through a plantar plate according to claim 4, wherein the step of obtaining a plantar plate repair device comprises obtaining a plantar plate repair device wherein the guide further includes a gripping structure comprising at least one of notches and indentations on sides of the guide to facilitate gripping during sliding movement of the guide.

13. The method of passing a suture through a plantar plate according to claim 4, wherein the step of obtaining a plantar plate repair device comprises obtaining a plantar plate repair device wherein the width of the shaft, the guide, and the footprint is equal to or wider than the plantar plate and in the range of 14 mm to 16 mm.

14. The method of passing a suture through a plantar plate according to claim 4, wherein the step of obtaining a plantar plate repair device comprises obtaining a plantar plate repair device wherein a handle extends from the shaft proximate an end opposite the footprint and further comprising the step of grasping the handle to support the shaft.

15. The method of passing a suture through a plantar plate according to claim 14, wherein the step of obtaining a plantar plate repair device comprises obtaining a plantar plate repair device wherein the handle projects between 90 and 150 degrees from the shaft.

16. The method of passing a suture through a plantar plate according to claim 1, wherein the step of obtaining a plantar plate repair device comprises obtaining a plantar plate repair device wherein the guide further includes gripping formations comprising gripping teeth, on an operatively lower surface of the guide.

17. The method of passing a suture through a plantar plate according to claim 1, wherein the step of obtaining a plantar plate repair device comprises obtaining a plantar plate repair device wherein the shaft and footprint are formed from a flat sheet of surgical steel.

18. A method of passing a suture through a plantar plate comprising the steps of:
  obtaining a plantar plate repair device comprising a shaft with a length, a footprint projecting away from the shaft at an angle to the shaft length, and a guide;
  placing the footprint underneath the plantar plate such that the plantar plate is located against the footprint;
  changing a relationship between the footprint and the guide so that the plantar plate is operatively stabilized between the footprint and the guide; and
  with the plantar plate stabilized, passing a length of a suture through the plantar plate,
  wherein the footprint defines an opening, the step of passing a length of a suture through the plantar plate comprises using a needle to pass the suture through the opening in the footprint, the step of changing a relationship between the footprint and the guide comprises sliding the guide on the shaft to operatively clamp the plantar plate between the guide and the footprint, and wherein the guide further defines at least one needle receiving guide hole for operatively guiding the needle through the opening in the footprint as the length of suture from the needle is passed through the plantar plate,
  wherein the step of obtaining a plantar plate repair device comprises obtaining a plantar plate repair device wherein the shaft is provided with a slot disposed substantially centrally on the shaft, which operatively receives gripping formations of the guide to allow sliding of the guide within the slot and along the shaft,
  wherein the step of obtaining a plantar plate repair device comprises obtaining a plantar plate repair device with a graspable handle and wherein the slot is enlarged proximate the handle such that the guide is slidably insertable thereinto and removable therefrom.

19. A method of passing a suture through a plantar plate comprising the steps of:
  obtaining a plantar plate repair device comprising a shaft with a length, a footprint projecting away from the shaft at an angle to the shaft length, and a guide;
  placing the footprint underneath the plantar plate such that the plantar plate is located against the footprint;
  changing a relationship between the footprint and the guide so that the plantar plate is operatively stabilized between the footprint and the guide; and
  with the plantar plate stabilized, passing a length of a suture through the plantar plate,
  wherein the footprint defines an opening, the step of passing a length of a suture through the plantar plate comprises using a needle to pass the suture through the opening in the footprint, the step of changing a relationship between the footprint and the guide comprises sliding the guide on the shaft to operatively clamp the plantar plate between the guide and the footprint, and wherein the guide further defines at least one needle receiving guide hole for operatively guiding the needle through the opening in the footprint as the length of suture from the needle is passed through the plantar plate,
  wherein the step of obtaining a plantar plate repair device comprises obtaining a plantar plate repair device wherein the at least one needle receiving guide hole of the guide comprises a pair of connected receiving guide holes for operatively guiding a pair of needles through the opening in the footprint to loop the length of the suture from the pair of needles through the plantar plate.

20. A method of passing a suture through a plantar plate comprising the steps of:
  obtaining a plantar plate repair device comprising a shaft with a length, a footprint projecting away from the shaft at an angle to the shaft length, and a guide;
  placing the footprint underneath the plantar plate such that the plantar plate is located against the footprint;
  changing a relationship between the footprint and the guide so that the plantar plate is operatively stabilized between the footprint and the guide; and
  with the plantar plate stabilized, passing a length of a suture through the plantar plate,
  wherein the footprint defines an opening, the step of passing a length of a suture through the plantar plate comprises using a needle to pass the suture through the opening in the footprint, the step of changing a relationship between the footprint and the guide comprises sliding the guide on the shaft to operatively clamp the plantar plate between the guide and the footprint, and wherein the guide further defines at least one needle receiving guide hole for operatively guiding the needle through the opening in the footprint as the length of suture from the needle is passed through the plantar plate,
  wherein the step of passing a length of a suture through the plantar plate comprises passing opposite ends of the length of the suture through the at least one needle receiving guide hole, the plantar plate and the opening in the footprint respectively to form a suture loop and further comprises a first step of passing one of the opposite ends of the length of the suture through the at least one needle receiving guide hole, plantar plate and the opening in the footprint, and a second step of re-aligning the device relative to the plantar plate and passing the other of the opposite ends of the length of the suture through the at least one needle receiving guide hole, the plantar plate, and the opening in the footprint.

21. A method of passing a suture through a plantar plate comprising the steps of:
  obtaining a plantar plate repair device comprising a shaft with a length, a footprint projecting away from the shaft at an angle to the shaft length, and a guide;
  placing the footprint underneath the plantar plate such that the plantar plate is located against the footprint;

changing a relationship between the footprint and the guide so that the plantar plate is operatively stabilized between the footprint and the guide;

with the plantar plate stabilized, passing opposite ends of a length of a suture through the plantar plate and the footprint to form a suture loop; and moving the footprint and the opposite ends of the suture from below the plantar plate and pulling said footprint dorsally to thereby pull the opposite ends of the suture to above the plantar plate.

\* \* \* \* \*